(12) United States Patent  
Osman (10) Patent No.: US 7,741,845 B2  
(45) Date of Patent: Jun. 22, 2010

(54) IMAGING TISSUE DEFORMATION USING STRAIN ENCODED MRI

(75) Inventor: Nael F. Osman, Balitmore, MD (US)

(73) Assignee: Johns Hopkins University, Baltimore, MD (US)

( * ) Notice: Subject to any disclaimer, the term of this patent is extended or adjusted under 35 U.S.C. 154(b) by 237 days.

(21) Appl. No.: 11/658,011

(22) PCT Filed: Jul. 22, 2005

(86) PCT No.: PCT/US2005/026358

§ 371 (c)(1),
(2), (4) Date: Aug. 28, 2008

(87) PCT Pub. No.: WO2006/012623

PCT Pub. Date: Feb. 2, 2006

(65) Prior Publication Data

US 2008/0315877 A1      Dec. 25, 2008

Related U.S. Application Data

(60) Provisional application No. 60/590,289, filed on Jul. 22, 2004.

(51) Int. Cl.
*G01V 3/00* (2006.01)
(52) U.S. Cl. ...................... 324/309; 324/307
(58) Field of Classification Search ......... 324/300–345; 600/407–445
See application file for complete search history.

(56) References Cited

U.S. PATENT DOCUMENTS

| 5,524,636 A | 6/1996 | Sarvazyan et al. |
| 6,030,344 A * | 2/2000 | Guracar et al. .............. 600/447 |
| 6,270,459 B1 * | 8/2001 | Konofagou et al. ......... 600/449 |
| 2005/0054910 A1 * | 3/2005 | Tremblay et al. ........... 600/411 |

OTHER PUBLICATIONS

Sampath et al: Imaging the evolution of three-dimensional myocardial strains using a fast MR imaging technique, IEEE, pp. 624-627 (2004).*

* cited by examiner

*Primary Examiner*—Brij B Shrivastav
(74) *Attorney, Agent, or Firm*—McKenna Long & Aldridge LLP (57) ABSTRACT

Disclosed is a system and method for imaging strain of tissue, such as the heart, in a quantitative manner. The present invention provides images of strain, which corresponds to heart function, by tagging a tissue region of interest, and acquiring multiple images by tuning an MRI RF receiver to frequencies above and below the tagging frequency. Depending on the tagging spatial frequency, and the spread between the high- and low-tuning frequencies, linear measurements of strain may be made on a pixel by pixel basis. By selectively tagging the tissue of interest by use of selective excitation, images may be acquired sufficiently fast to provide anatomical and functional imagery within a single heartbeat. By acquiring additional images, dead tissue may be differentiated from contracting tissue as well as blood.

21 Claims, 12 Drawing Sheets

IMAGING TISSUE DEFORMATION USING STRAIN ENCODED MRI

This application claims the benefit of U.S. Provisional Patent Application No. 60/590,289, filed on Jul. 22, 2004; and U.S. Provisional Patent Application No. 60/651,368 filed on Feb. 9, 2005, which are hereby incorporated by reference for all purposes as if fully set forth herein.

BACKGROUND OF THE INVENTION

1. Field of the Invention

The present invention involves the field of Magnetic Resonance Imaging (MRI). More particularly, the present invention involves a system and method for imaging regional deformation of tissue.

2. Discussion of the Related Art

Improvements in medical imaging technologies, such as MRI and ultrasound, have made it possible to image internal anatomical features in ways that show both structure and motion. Better diagnosis of certain medical conditions, such as heart disease, generally requires imagery that may be acquired quickly, and that provides information pertaining to both anatomical structure as well as function. Accordingly, there is an ongoing need for quantitative imaging of various tissue regions, such as the heart or other organs, which are observer independent. As used herein, observer independence means that the images capture the tissue as it nominally functions and involves minimal interaction with the mode of imaging. MRI is a good example of observer independent imaging.

As an example, observer-independent quantitative imaging of regional deformations in muscle tissue, such as the heart, may better enable diagnosis of coronary disease. Further, observer-independent quantitative imaging for tissue characterizations such as elastography may enable identification of tumors in surrounding tissue where it is impractical to apply external pressure, such as the chest cavity.

Magnetic Resonance Imaging (MRI) has become a leading means of imaging for noninvasive diagnostics. By operating in regions of the electromagnetic spectrum that are benign to tissue, MRI imagery may be acquired repeatedly without danger to the patient. Also, the advent of vast and relatively inexpensive computational power has enabled MRI imagery to be acquired in real time or near real time. Further, advances in MRI pulse sequencing, gradient magnet control, and signal processing algorithms have improved the volumetric spatial resolution and dynamic range of acquired imagery. As used herein, the term "imagery" may refer to a single image or multiple images.

Related art approaches to strain imaging include Strain Encoded imaging (SENC), which is an MRI technique for imaging regional deformation of tissue, such as the heart muscle. However, related art developments in MRI, such as SENC imaging, are not able to provide high quality imagery of tissue that includes a quantitative measure of tissue deformation.

Non-MRI medical imaging technologies are generally not well suited for observer-independent imaging. These technologies, such as ultrasound, may involve invasive devices or cutaneous probes that may apply pressure to the patient's body in the vicinity of the tissue being imaged. As such, other imaging technologies may interfere with the function of certain organs by applying pressure, causing tissue deformations that may interfere with the motion and function of the tissue being imaged.

Quantitative imagery of tissue deformation requires the ability to provide sufficient dynamic range of deformation. As used herein, dynamic range refers to resolution and linearity in frequency and intensity. Further, providing quantitative deformation imagery for different tissue types requires the ability to adaptively select the appropriate dynamic range for the tissue region of interest.

SUMMARY OF THE INVENTION

Accordingly, the present invention is directed to imaging tissue deformation using strain encoded MRI that substantially obviates one or more of the problems due to limitations and disadvantages of the related art.

An advantage of the present invention is that it provides a more direct, observer-independent method for assessing tissue deformation, such as regional function of the heart muscle. As used herein, regional function refers to the function of a localized section of the tissue, such as a ventricle and its surrounding tissue.

Another advantage of the present invention is that it provides improved MRI imagery of anatomy and tissue strain.

Another advantage of the present invention is that it improves the dynamic range of MRI strain imaging.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, a method for acquiring strain images of a tissue is provided, which comprises transmitting a tagging pulse having a spatial tagging spatial frequency; receiving a first RF signal corresponding to a first receive spatial frequency that is below the tagging spatial frequency; receiving a second RF signal corresponding to a second receive spatial frequency that is above the tagging spatial frequency; and computing a strain value corresponding to the received first RF signal and the received second RF signal.

In another aspect of the present invention, a system for acquiring strain imaging of a tissue is provided, which comprises a gradient coil; an RF coil; an RF demodulator; and a processor having a computer readable medium encoded with a program for transmitting a tagging pulse having a tagging spatial frequency; receiving a first RF signal corresponding to a first receive spatial frequency that is below the tagging spatial frequency; receiving a second RF signal corresponding to a second receive spatial frequency that is above the tagging spatial frequency; and computing a strain value corresponding to the received first RF signal and the received second RF signal.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIGS. 9A-15B illustrate slice-selection encoding schemes for reducing the field of view of tagging.

DETAILED DESCRIPTION OF THE ILLUSTRATED EMBODIMENTS

The present invention involves strain imaging of muscle tissue, including myocardial (heart) tissue, by providing a sequence of strain encoded imaging (SENC) pulse sequences having a tagging spatial frequency, each of which is followed by a sequence of tuned MR imaging pulse sequences (explained below). The subsequent tuned MR imaging sequences acquires MR data at specific tuning frequencies that are located above and/or below the tagging spatial frequency used in SENC imaging. By selecting an appropriate tagging spatial frequency and the spectral differences between the tagging spatial frequency and the higher and lower tuning frequencies, strain imaging can be obtained with a dynamic range sufficient for quantitative analysis of strain.

Although the discussion below pertains to imaging the heart, it will be readily apparent to one of ordinary skill that the discussion may apply to any tissue region in which quantitative images of strain are desired.

Figure 1:
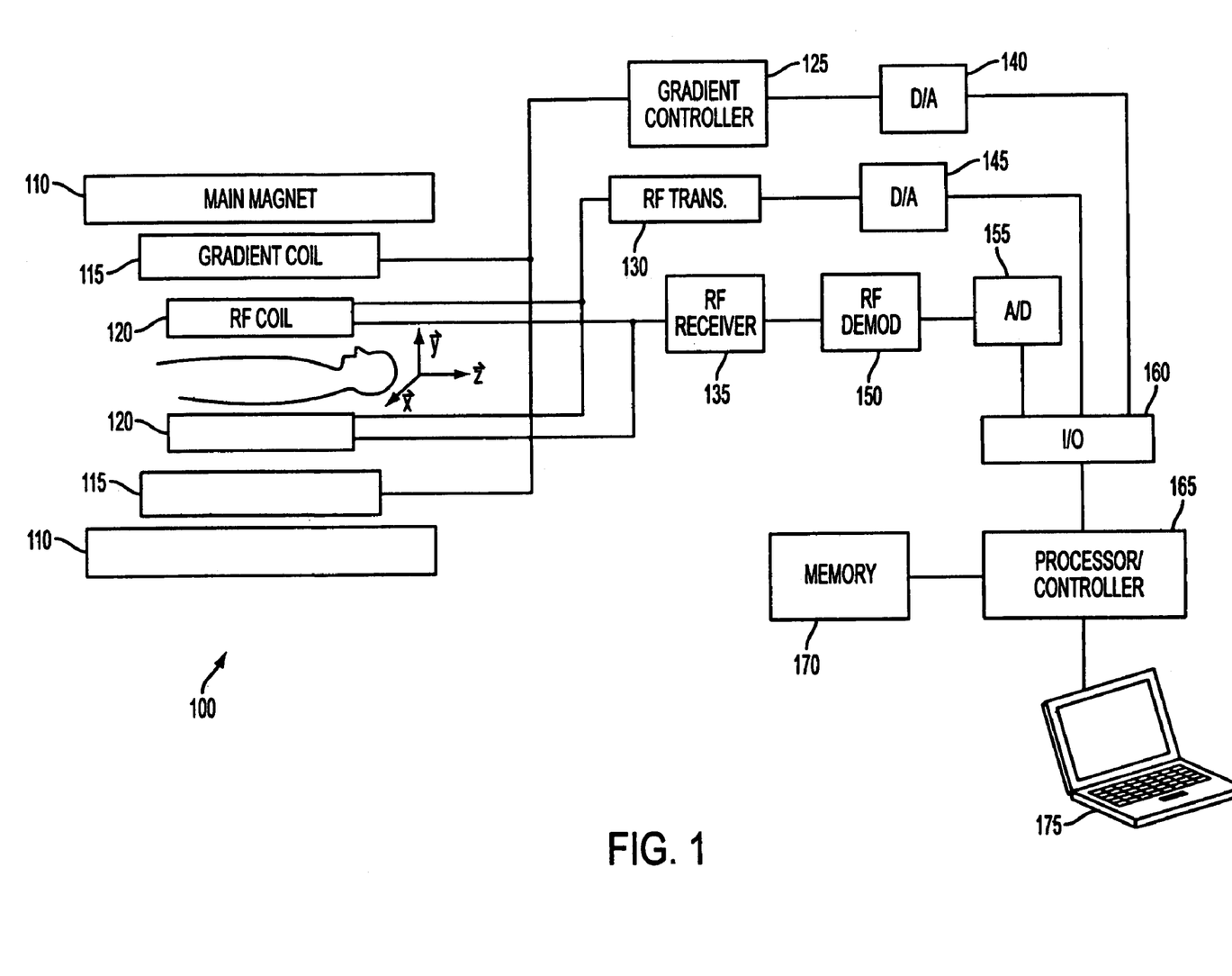
FIG. 1 illustrates an exemplary system for imaging tissue deformation using strain encoded MRI according to the present invention.

FIG. 1 illustrates an exemplary system 100 according to the present invention. System 100 includes a main magnet 110; a gradient coil 115; an RF coil 120; and a processor/controller 165 having a memory 170, an input/output (I/O) module, and a user interface 175. The gradient coil 115 is connected to a gradient controller 125, which is connected to a digital to analog (D/A) converter 140. The RF coil 120 is connected to an RF transmitter 130 and an RF receiver amplifier 135, both of which are respectively connected to analog to digital (A/D) converters 145 and 155. The A/D converters 145 and 155, and the D/A converter 140, are connected to the processor/controller 165 via the I/O module 160.

The processor/controller 165, along with the memory 170 and user interface 175, may include one or more computers that may be co-located with the other components of system 100, or may include computers and databases that are located remotely and connected over a network. The memory 170 may be integrated into the processor/controller 165, or may be distributed across multiple computers in different locations. It will be readily apparent to one of ordinary skill that multiple architectures for the processor/controller, and memory 170, the I/O module 160, and the user interface 175 are possible and within the scope of the invention.

The memory 170 contains software (hereinafter the "software"), which contains instructions, data, and configuration parameters for performing the processes of the present invention.

All or part of system 100 may be a commercially available MRI system, such as those manufactured by General Electric Medical Systems, Siemens, Philips, or Toshiba. The software may be stored in memory 170, and run on the processor/controller 165 that is integral to a commercially available MRI system. Alternatively, the memory 170 and processor/controller 165 that stores and executes the software may be external to the commercially available MRI system, and may communicate with the MRI system's computer over a network.

Figure 2:
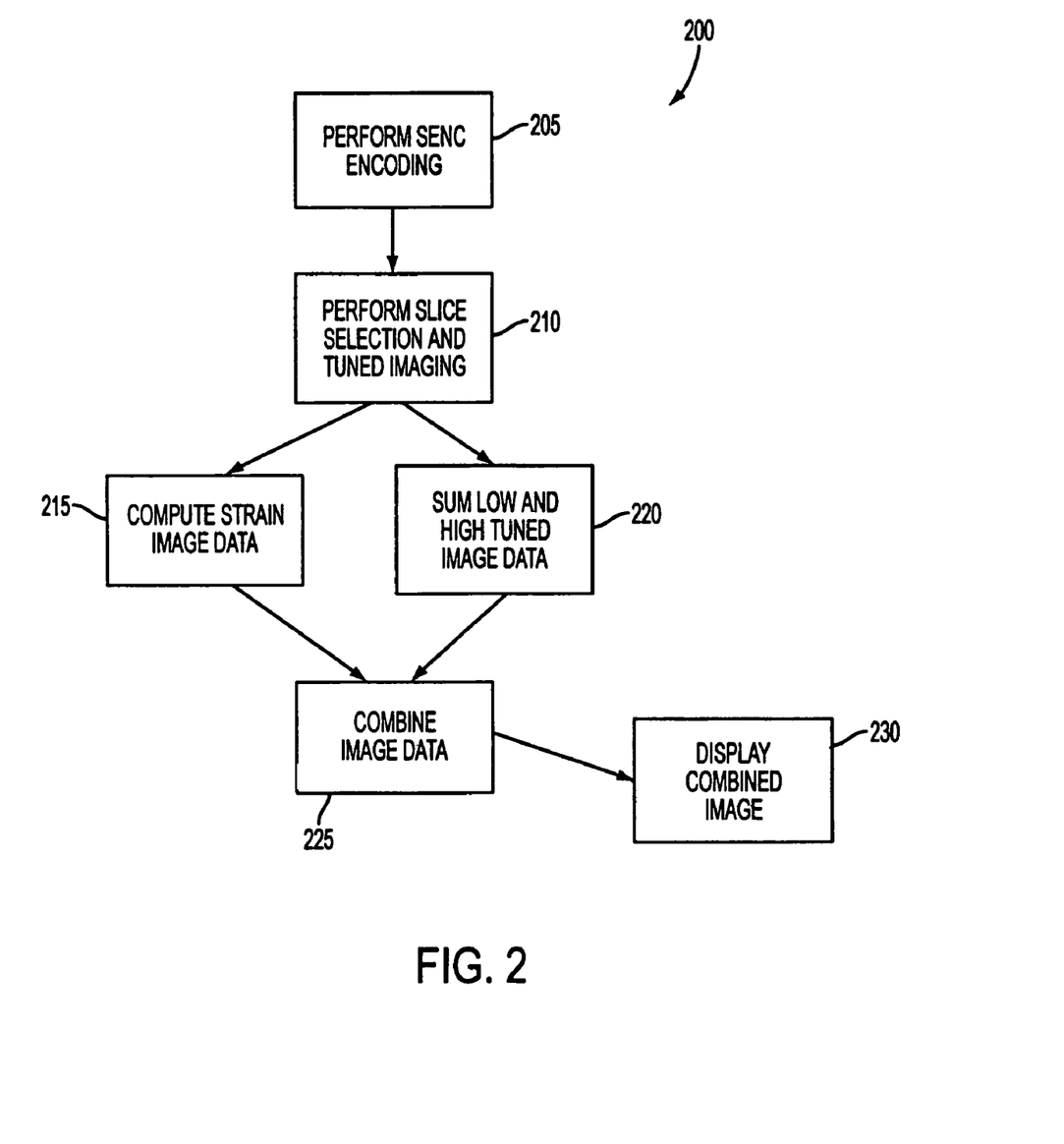
FIG. 2 illustrates an exemplary process for imaging tissue deformation using strain encoded MRI according to the present invention.

FIG. 2 illustrates an exemplary process 200 for imaging tissue deformation according to the present invention. Process 200 may be performed in an automated fashion by the software, or may involve user interaction between the software and the user via the user interface 175.

Referring to FIG. 2, strain encoding (SENC) is performed in step 205, in which the region of interest in the muscle is "tagged" with a sinusoidal gradient having a tagging spatial frequency $\omega_0$. Strain encoded imaging and tagging are discussed in U.S. Pat. No. 6,892,089, CARDIAC MOTION TRACKING USING CINE HARMONIC PHASE (HARP) MAGNETIC RESONANCE IMAGING; and U.S. Pat. No. 6,597,953, METHOD FOR HARMONIC PHASE MAGNETIC RESONANCE IMAGING, which are incorporated by reference as if fully set forth herein.

Figure 3:
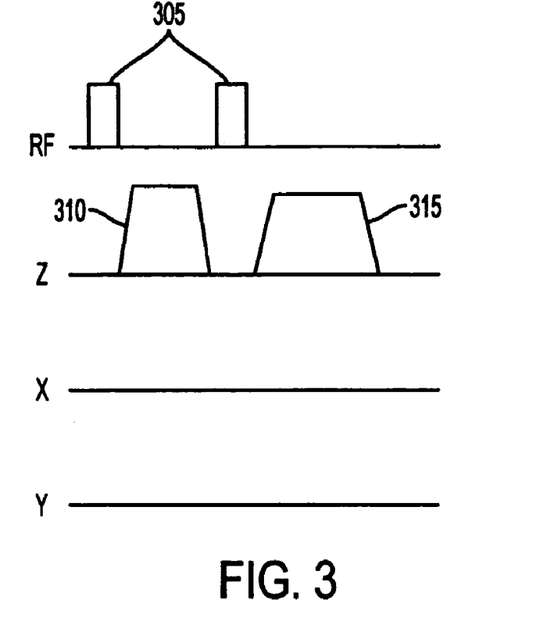
FIG. 3 illustrates an exemplary strain encoded imaging (SENC) pulse sequence according to the present invention.

FIG. 3 illustrates an exemplary set of signals issued in step 205. In step 205, the software in memory 170 issues commands to send at least two 90° pulses 305 to the RF transmitter 130 via the I/O port 160 and the D/A converter 145. The RF transmitter 130 sends the corresponding signals to the RF coil 120. The software also issues commands to send a gradient pulse 310 along the z-axis between the two 90° pulses 305. In doing so, the software sends data values to the gradient controller 125 via the D/A converter 140 and the I/O port 160. The gradient controller 125 then sends the corresponding signals to the gradient coil 115, which emits a magnetic field corresponding to the gradient pulse 310 along the z-axis.

After the second of the 90° pulses 305, the software issues a command to send a crusher gradient pulse 315 along the z-axis. As used herein, crusher gradient pulse 315 refers to a gradient pulse emitted along the z-axis, which destroys any magnetization in the transverse plane (defined by the x and y-axes) to prevent any unwanted coherences remaining from the gradient pulse 310. In doing so, the crusher gradient pulse 315 mitigates image artifacts.

Further in accordance with step 205, the software commands the gradient controller 125 to send the gradient pulse 310 at a reference time. An exemplary reference time may be immediately after the R-wave of an echocardiogram at end-diastole, which will enable subsequent tuned imaging to be done during the range of heart motion.

In step 210, slice selection and tuned imaging is performed, in which the software iteratively transmits slice-selection RF pulses and gradient pulses while receiving RF energy emitted by the tissue region activated by the RF and gradient pulses at a tuning frequency, which is either greater than ($\omega_H$) or less than ($\omega_L$) the tagging spatial frequency $\omega_0$. The relative locations of $\omega_H$ and $\omega_L$ are described below.

Figure 4:
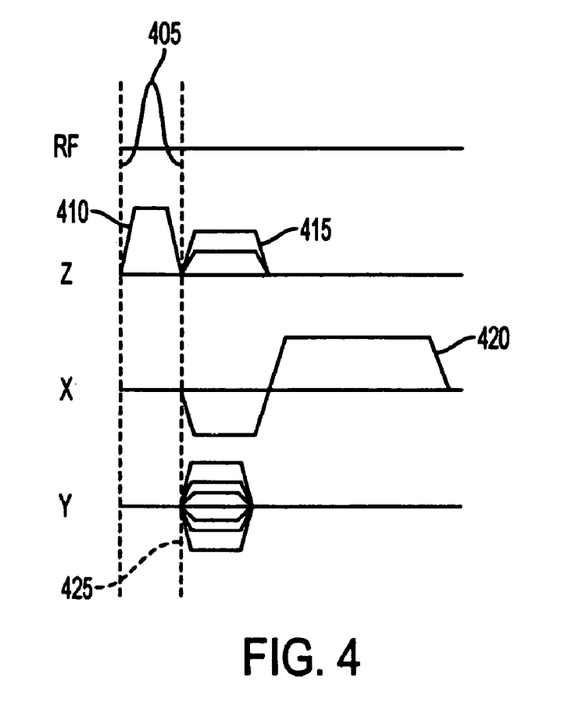
FIG. 4 illustrates an exemplary slice selection and tuned imaging pulse sequence according to the present invention.
Figure 5:
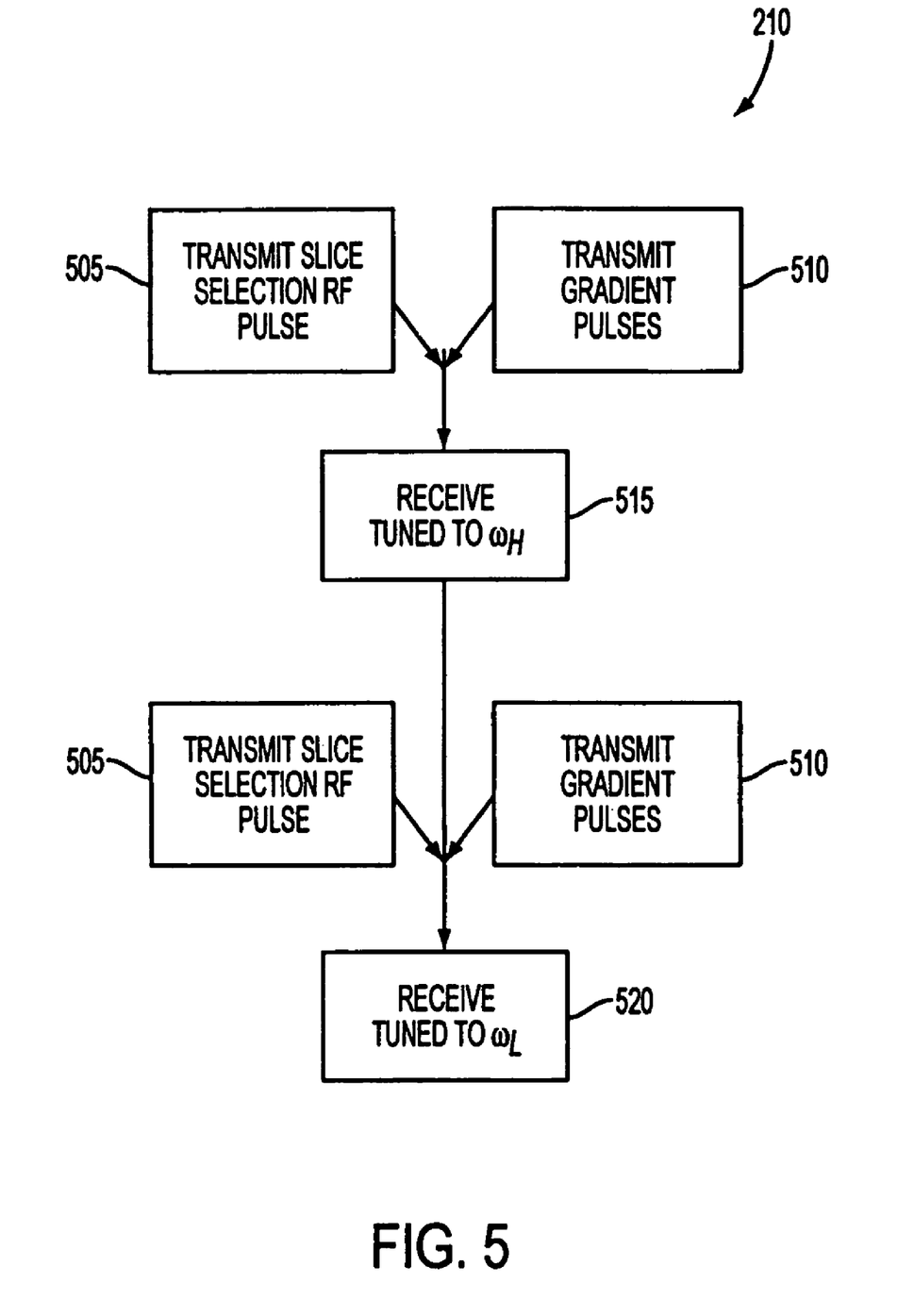
FIG. 5 illustrated an exemplary process for performing slice selection and tuned imaging.

FIG. 4 illustrates an exemplary set of signals, including RF and gradient pulses, issued in step 210; and FIG. 5 illustrates an exemplary subprocess for step 210. In step 505, the software issues commands to send a slice-selection RF pulse 405 to the RF transmitter 130 via the I/O port 160 and the D/A converter 145. The RF transmitter 130 sends the corresponding signals to the RF coil 120. In step 510, the software issues commands to send a gradient pulse 410 along the z-axis, the frequency encoding gradient 420 along the x-axis, and the phase encoding gradient 425 along the y-axis.

In step 515, the software further issues commands to the RF receiver 135 and the RF demodulator 150 to receive the RF energy being emitted by the tissue region activated by the RF pulse 405 and the gradient pulses 410, 420, and 425. The software provides the RF demodulator 150 with a high tuning frequency $\omega_H$, which is greater than the tagging spatial frequency $\omega_0$ by a predetermined frequency difference. The software receives the demodulated RF signal via the A/D converter 155 and the I/O port 160 and stores the corresponding data values in memory 170. Based on the frequency encoding provided by gradient pulse 420, and the phase encoding provided by gradient pulse 425, the RF signal received at high tuning frequency $\omega_H$ and stored by the software is spatially encoded such that a 2-D image (in the transverse plane defined by the x and y-axes) of a "slice" along the z-axis, which is defined by the z-axis tuning gradient pulse 415, is acquired and stored in memory 170. Accordingly, the stored data values correspond to each pixel in the 2-D image.

The tuning gradient pulse 415, depending on whether the low tuning frequency $\omega_L$ or the high tuning frequency $\omega_H$ is to be received, may conform to either of the following relations:

$$\omega_L = \gamma \int G_L(t)dt \text{ or } \omega_H = \gamma \int G_H(t)dt$$

where $\gamma$ is the gyromagnetic ratio for the protons in the slice-selected tissue, $G_L(t)$ is the tuning gradient pulse 415 correspond to the low tuning frequency $\omega_L$, and $G_H(t)$ is the tuning gradient pulse 415 corresponding to the high tuning frequency $\omega_H$.

Next in the exemplary subprocess illustrated in FIG. 5, steps 505 and 510 are repeated, and RF energy is received and stored in step 520 in a manner similar to step 515. However, in step 520, the software commands the RF demodulator 150 to use a low tuning frequency $\omega_L$, which is lower than the tagging spatial frequency $\omega_0$ by a predetermined frequency difference. At the end of step 210, the software has stored data values for each pixel within two images, corresponding to RF energy sensed by the RF coil 120 and received at a tuning frequencies $\omega_L$ and $\omega_H$.

Figure 6:
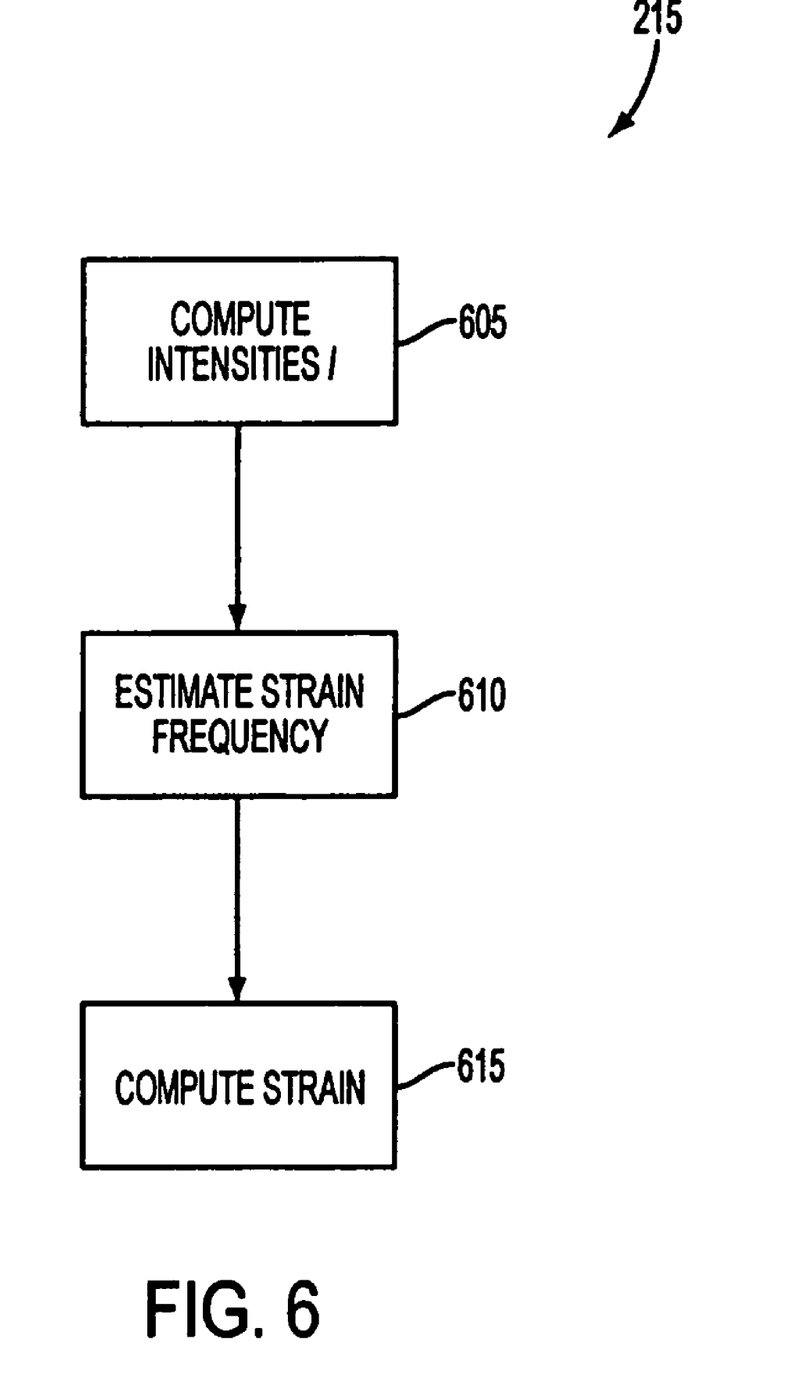
FIG. 6 illustrates an exemplary process for computing strain using collected image data.

In step 215, the software computes strain corresponding to each pixel within the 2-D images stored in step 210. FIG. 6 illustrates an exemplary process for implementing step 215.

In step 605, the software computes the intensity of the RF signal received on a pixel-by-pixel basis for each receive spatial frequency according to the following relation:

$$I(y,t,\omega_H) = \rho(y,t)S(\omega(y,t) - \omega_H),$$

where I is the RF signal intensity; y is the pixel location; $\rho(y,t)$ is the proton density at location y; $S(\omega(y,t) - \omega_H)$ is the Fourier transform of the pixel profile derived from the envelope of the slice-selection RF pulse 405; and $\omega(y,t)$ is the local spatial frequency in the slice-selected volume of tissue in response to the slice-selection RF pulse 405.

The strain frequency is estimated in step 610. As discussed earlier, by combining image data for two separate tunings $\omega_L$ and $\omega_H$, the strain frequency, which is the spatial frequency of the tagged slice-selected volume, may be estimated. The frequency shift from the tagging spatial frequency $\omega_0$ to the strain frequency corresponds to strain, is computed on a pixel-by-pixel basis by combining the intensities computed (above) as follows:

$$\hat{\omega}(y,t) = \frac{\omega_L I(y,t;\omega_L) + \omega_H I(y,t;\omega_H)}{I(y,t;\omega_L) + I(y,t;\omega_H)}.$$

The strain frequency $\hat{\omega}(y,t)$ is an estimate because the "true" center frequency of the RF energy emitted by the slice-selected volume may not be the same as $\hat{\omega}(y,t)$, based in part on the geometry of the slice-selected volume. The estimated strain frequency $\hat{\omega}(y,t)$ is most accurate in the case of a rectangular slice profile.

In step 615, the software computes the strain on a pixel-by-pixel, based on the estimated strain frequency $\hat{\omega}(y,t)$. The strain may be determined (in %) from the change in local frequency as follows:

$$\varepsilon(y,t) = \left(\frac{\omega_0}{\hat{\omega}(y,t)} - 1\right) \times 100.$$

The accuracy of the computation of $\epsilon(y,t)$ depends on the orientation of the imaging plane. As discussed herein, the imaging plane is the transverse plane defined by the x and y-axes.

One of ordinary skill will know how to implement the above equations in software using either a commercially available mathematical scripting language or by coding the equations in any number of computer languages.

The result of step 215 is an image indicating the amount of strain in the imaged volume. Each pixel within the 2-D image has a value corresponding to the percentage of strain that the tissue in that pixel is undergoing.

Figure 7A:
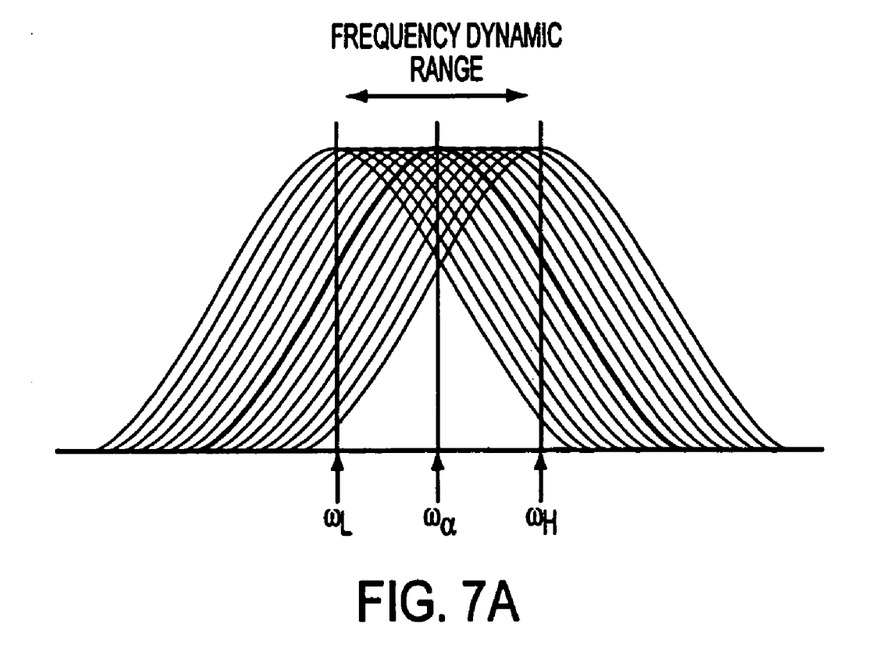
FIGS. 7A and 7B illustrate the dynamic range and linear intensity range of measurement depending on the selection of the tagging spatial frequency and high and low tuning frequencies.
Figure 7B:
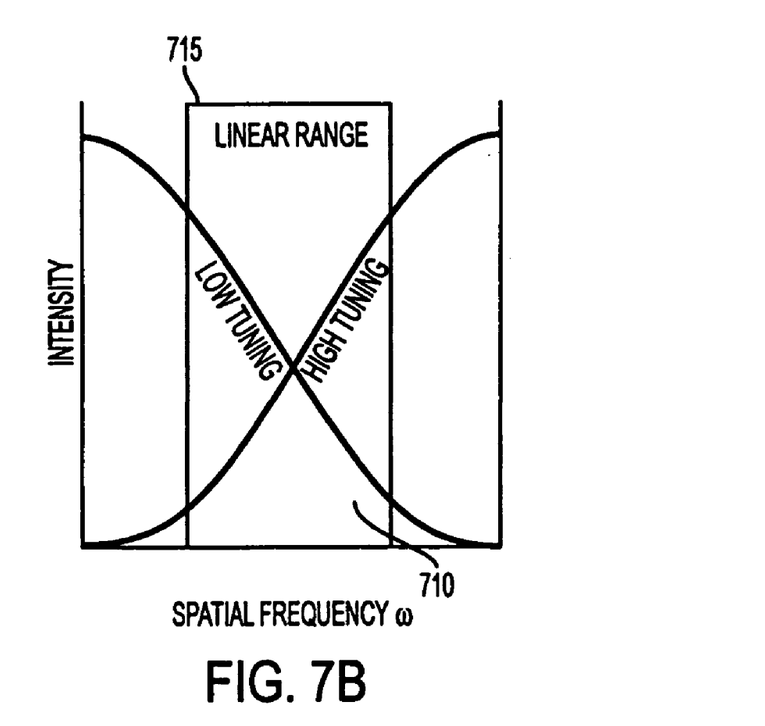

In step 220, the images acquired corresponding to the tuning frequencies $\omega_L$ and $\omega_H$ are summed. As illustrated in FIG. 7B, by summing the intensities of the RF signals received for both tuning frequencies $\omega_L$ and $\omega_H$, the overall intensity of the summation may be substantially constant. As such, the summed image will have good dynamic range, but substantially no strain features. As used herein, this summed image is referred to as an anatomical image, because it reveals the anatomy absent the strain-induced effects.

In step 225, the respective image products of step 215 and 220 are combined, overlaying the strain image (from step 215) on the anatomical image (from step 220). In step 230, the combined image is displayed on user interface 175 and may be stored in memory. In combining the images, the software may color code each pixel in the anatomical image based on strain. It will be readily apparent to one of ordinary skill that different display schemes are possible and within the scope of the invention.

Process 200 may be repeated with each iteration imaging a successive "slice" along the z-axis. At the end of a desired number of iterations, the software may combine the image products of step 225 into a 3-D image of the tissue region of interest. Through the user interface 175, a user may then obtain images of different image planes within the tissue region, which show the anatomy of the given plane along with the strain corresponding to each pixel.

Referring to step 210, the selection of the tagging spatial frequency $\omega_0$ and tuning frequencies $\omega_L$ and $\omega_H$ affects the dynamic range of the quantitative imaging of strain. FIGS. 7A and 7B illustrate the relation between the selection of frequencies and the resulting dynamic range. The frequencies should be selected so that the estimated strain frequency $\hat{\omega}(y,t)$ will lie within the linear range 715 of the frequency dynamic range illustrated in FIGS. 7A and 7B. Referring to FIGS. 7A and 7B, the greater the distance between $\omega_L$ and $\omega_H$, the greater the frequency dynamic range. However, as the spread between $\omega_L$ and $\omega_H$ increases, the area of the intensity overlap 710 diminishes, which affects the linearity of the measurement of the intensity of the RF signal received on a pixel-by-pixel basis. In general, the lower the tagging spatial frequency $\omega_0$, the greater the frequency dynamic range.

In general, when the tissue measured by a given pixel is contracting, the strain frequency $\hat{\omega}(y,t)$ increases (shifts to the right); and when the tissue is stretching, the strain frequency $\hat{\omega}(y,t)$ decreases (shifts to the left). By estimating the strain frequency based on both the high-tuning and low-tuning frequencies $\omega_L$ and $\omega_H$, the dynamic range of the intensity measurement remains substantially constant. Further, if the strain frequency $\hat{\omega}(y,t)$ is within the linear range 715, the precision of the strain frequency $\hat{\omega}(y,t)$ estimation is consistent.

Step 210 may be repeated, with each iteration having a different tagging spatial frequency $\omega_0$ and tuning frequencies $\omega_L$ and $\omega_H$. This may be done in cases where a slice-selected volume may have regions undergoing different levels of strain, and one tagging spatial frequency is not sufficient. Each iteration of step 210 is done at an imaging time relative to the reference time (described above) at which the SENC encoding is done in step 205. Multiple iterations of step 210 may depend on the speed of the processor/controller 165 and/or the duration of the SENC encoding magnetization. In general, SENC encoding magnetization lasts a fraction of a second, allowing multiple iterations of tuned imaging in step 210.

Figure 8:
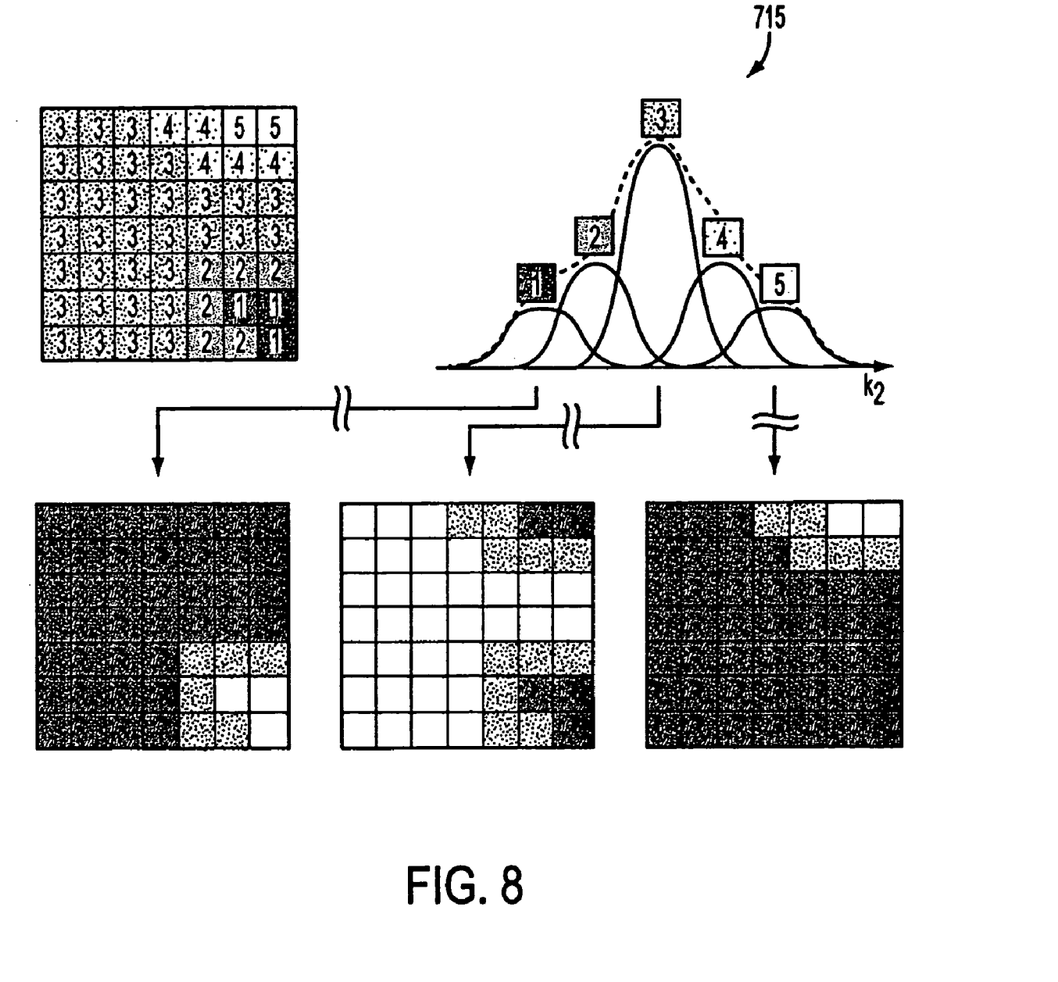
FIG. 8 illustrates an exemplary use of multiple tagging spatial frequencies and corresponding high and low tuning frequencies.

FIG. 8 illustrates the use of multiple tuning frequencies in cases where a slice-selected volume is undergoing different levels of strain. The plot of multiple frequency curves 810 shows different amplitudes of intensity, which corresponds to the proportions of the volume undergoing a certain strain. In other words, the tagging spatial frequency curve corresponding to the highest amplitude also corresponds to the level of strain that is prevalent in the slice-selected volume.

Referring to step 205, different forms of SENC encoding may be done within the scope of the present invention. For example, a smaller targeted volume may be tagged by the gradient pulse 310 in step 205. Tagging a smaller target volume as the effect of narrowing the field of view of the MRI system 100. By decreasing the tagged (SENC encoded) target volume, tuned images may be acquired more quickly, enabling faster acquisition of strain imagery according to the present invention. Accordingly, slice selected tagging may enable acquisition of strain in a region of the heart within a single heartbeat.

In employing slice selected tagging, the RF pulses of the tagging sequence are replaced with spatially selective ones to tag a limited volume. As a result, only the region that it is tagged will generate signal to be received with the low and high frequency tuned imaging iterations (of step 210).

FIGS. 9A to 15B show different examples of spatially selective tagging sequences that limit the tagging to different geometrical regions in the volume. The limiting of the tagging to smaller volumes helps to reduce the size of the imaged volume, which can be acquired faster.

Figure 9A:
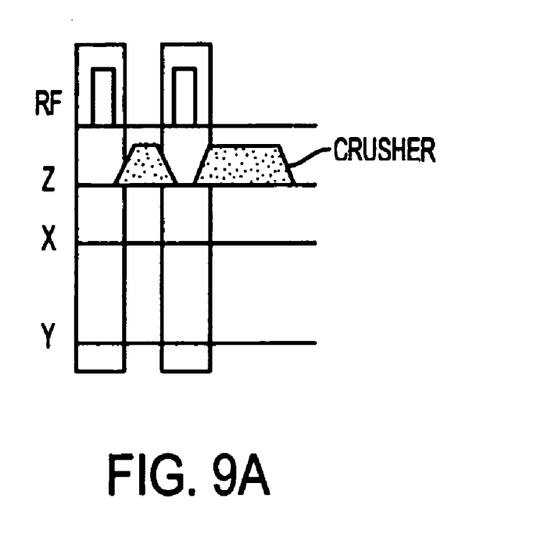
Figure 9B:
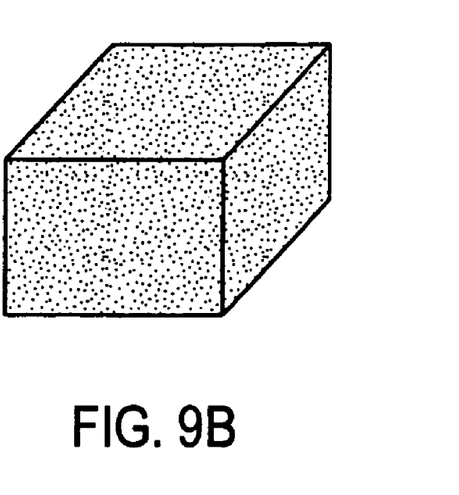

FIGS. 9A and 9B refer to the SENC encoding performed in step 205 as described above. In this exemplary case, tagging occurs in substantially the entire volume defined by the RF coil 120 of MRI system 100. The remainder of the exemplary encoding schemes, illustrated in FIGS. 10A-15B, limit the SENC encoded volume.

As used herein, by limiting the SENC encoded volume, the field of view of the MRI system 100 is reduced, and the volume of the excitation is limited.

Figure 10A:
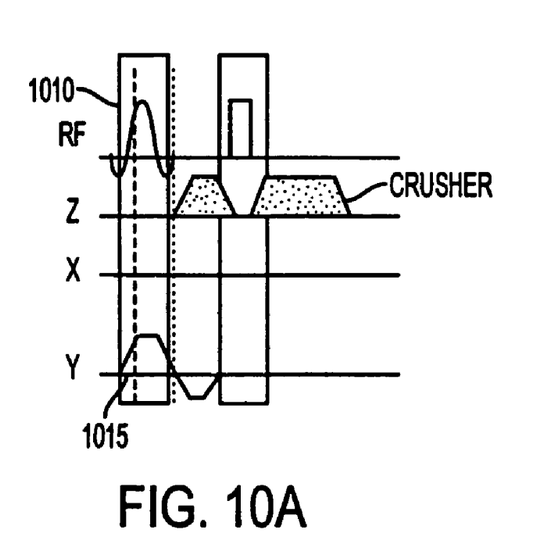
Figure 10B:
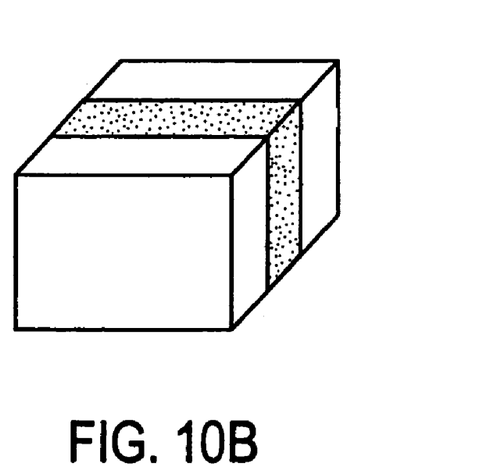

FIGS. 10A and 10B illustrate a slice-selected tagging scheme, referred to as 1D-1 SPAMM (Spatial Modulation of Magnetization), in which the RF tagging pulse 1010 limits strain encoding to a reduced field of view in the direction of the slice-selection gradient 1015 along the y-axis.

Figures 11A, 11B:
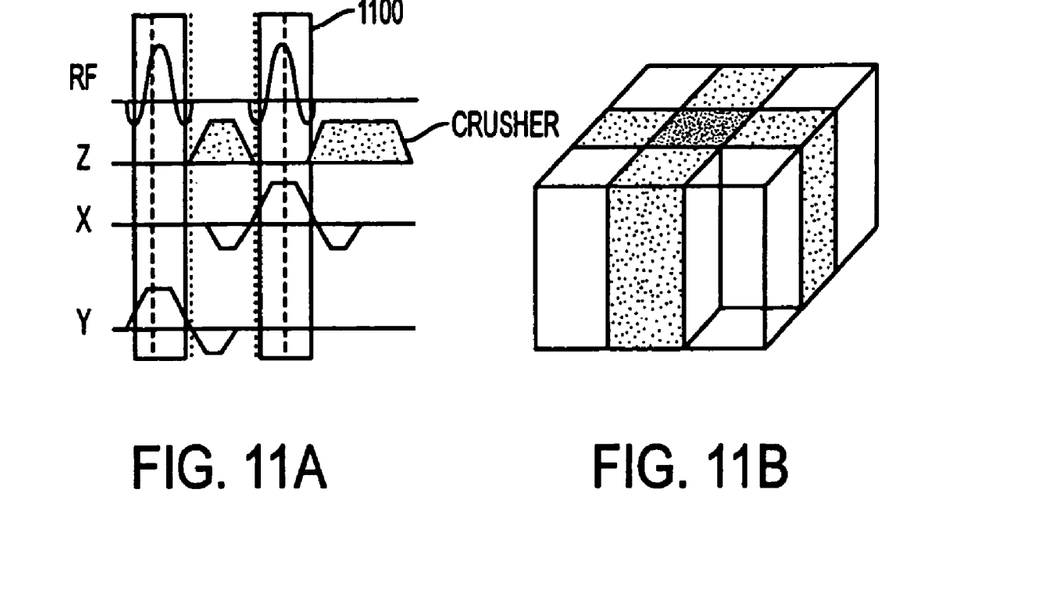

FIGS. 11A and 11B illustrate a slice-selected tagging scheme, referred to as 1D-1D SPAMM, which includes selective SENC magnetization along the x and y-axes using two RF excitations 1100. Under this slice-selected tagging scheme, the field of view of strain encoding is reduced in two directions.

Figures 12A, 12B:
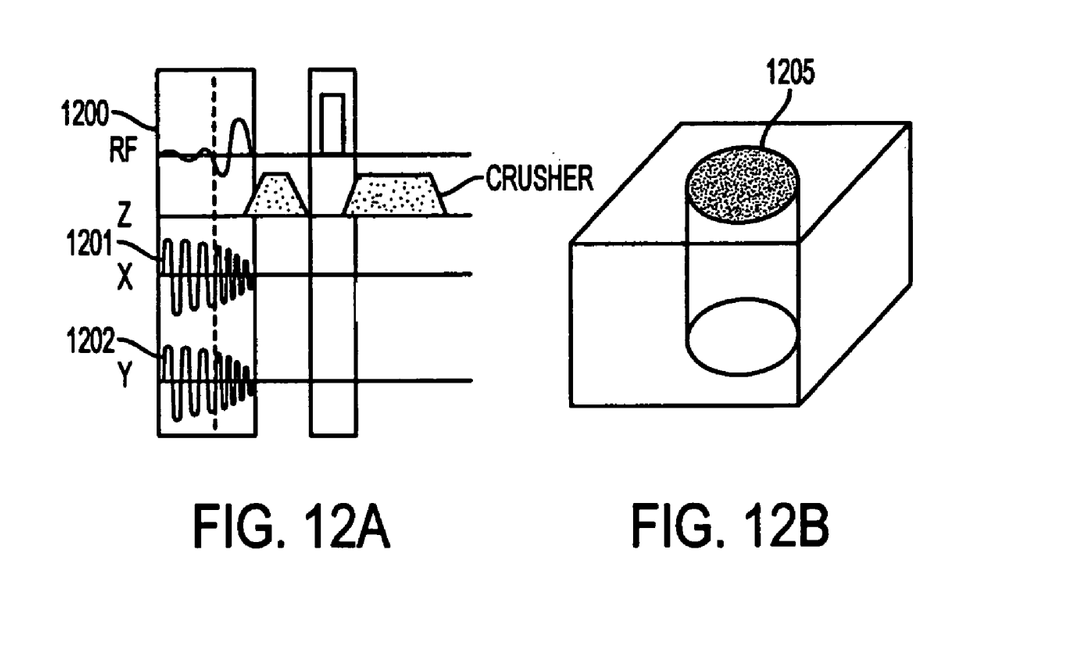

FIGS. 12A and 12B illustrate a slice-selected tagging scheme, referred to as 12D-1 SPAMM, in which a single RF pulse 1200 respectively having x and y components 1201 and 1202 tag a cylindrical volume 1205 of reduced field of view.

Figure 13A:
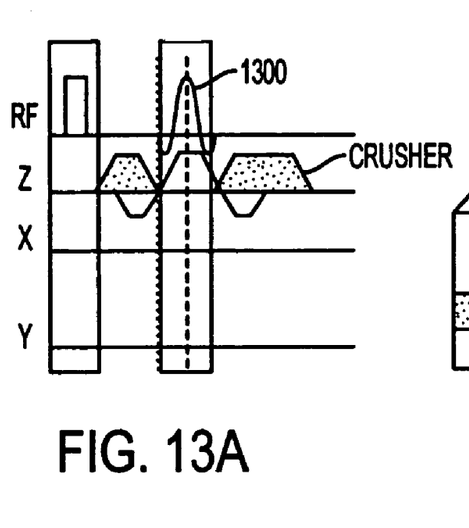
Figure 13B:
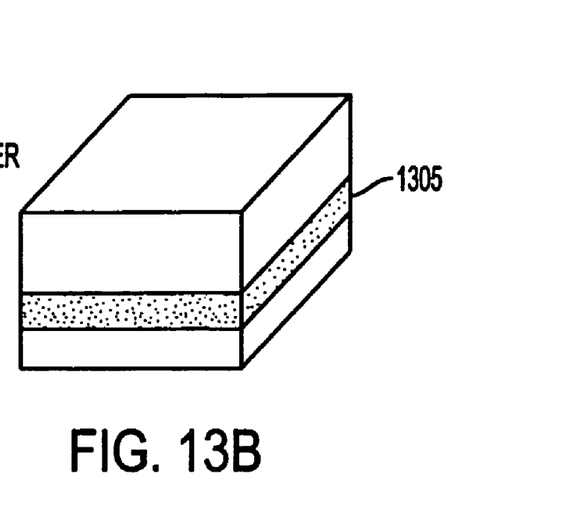

FIGS. 13A and 13B illustrate a 1-SF SPAMM slice-selected tagging scheme in which a second RF pulse 1300 limits the field of view along the z-axis, producing a thinner "slice" of excitation.

Figure 14A:
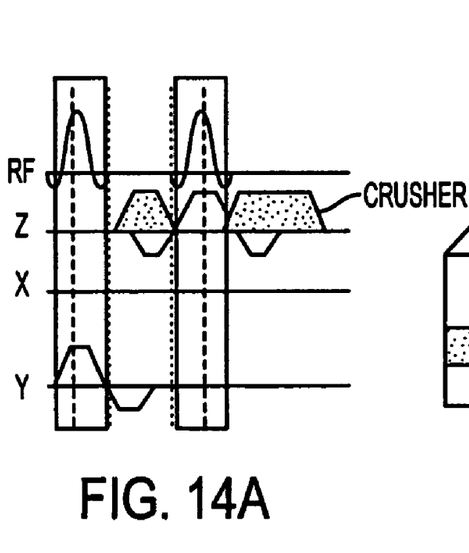
Figure 14B:
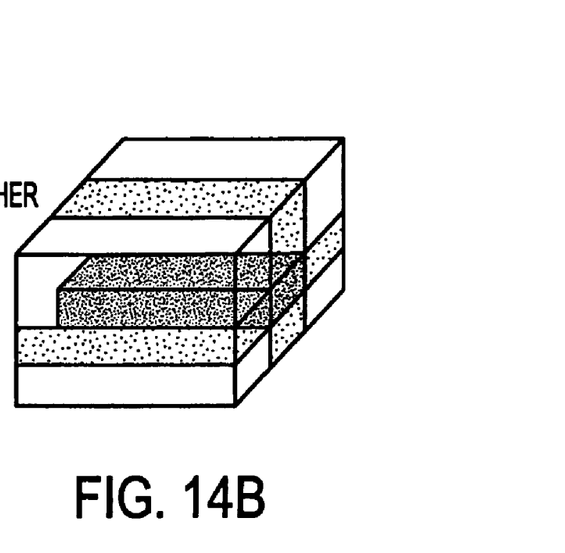

FIGS. 14A and 14B illustrate a 1D-SF slice-selected tagging scheme whereby the first RF pulse limits the field of view along the y-axis, and the second RF pulse limits the thickness of the field of view.

Figure 15A:
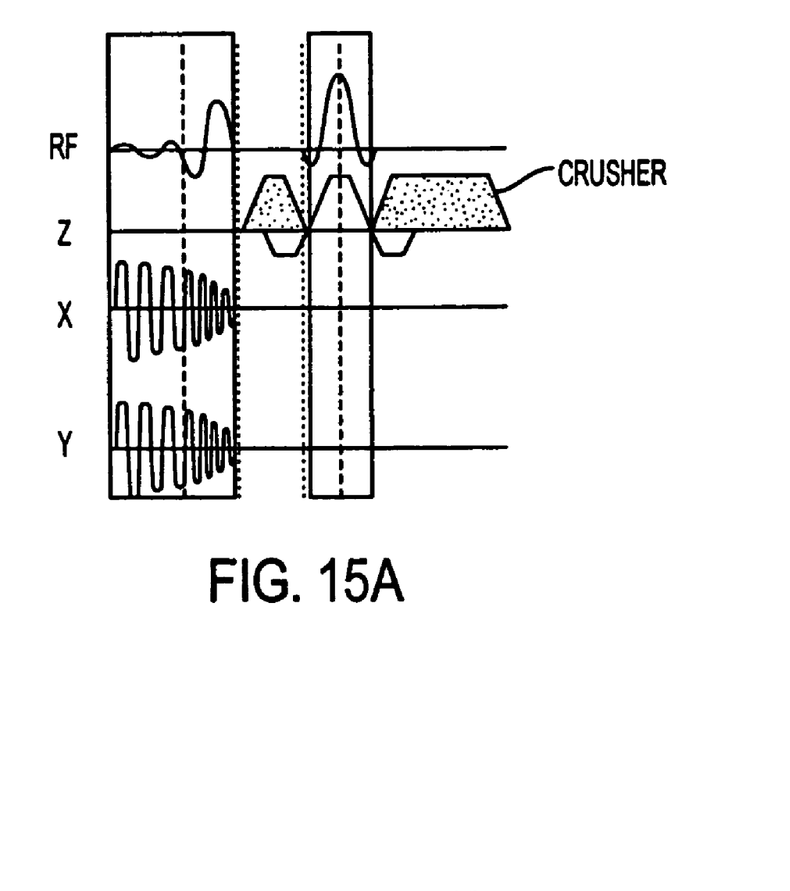
Figure 15B:
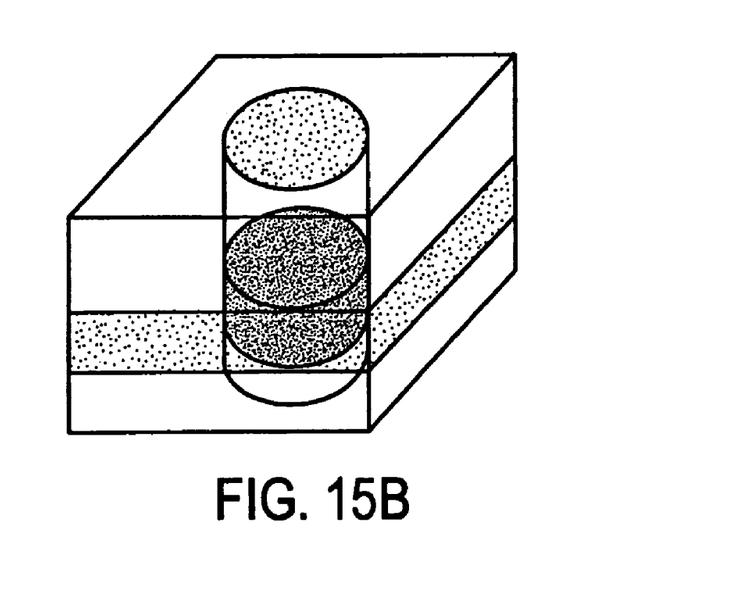

FIGS. 15A and 15B illustrate a 2D-SF SPAMM slice-selected tagging scheme whereby the single RF pulse illustrated in FIG. 12A is supplemented with a second RF pulse that limits the field of view along the z-axis, producing a thinner cylindrical field of view.

It should be noted that the present invention is not limited to strain imaging. It may also be used for other quantitative imaging applications, such as elastography. The imaging of strain with SENC can be used for imaging the tissue elasticity by combining the knowledge of the source of deformation with the pixel-by-pixel strain measurements described above. To perform elastography, an external source of pressure can be used to deform the tissue while the tissue is being imaged according to exemplary process 200 described above. In doing so, differences in tissue deformation may indicate differences in elasticity of the imaged tissue. By determining the volumetric contours of changes in elasticity, which may be obtained by multiple iterations of exemplary process 200 for different "slices" of tissue, tissue anomalies such as tumors may be identified in tissue.

It should also be noted that more than two tuning frequencies can be used according to the present invention for imaging other features or characteristics of the tissue other than strain. The SENC sequence can be used to image with more than two tuning frequencies for a given tagging spatial frequency $\omega_0$. For example, step 210, and its exemplary process illustrated in FIG. 5, may involve repeating steps 505 and 510, and adding another step similar to step 520, but with a different tune frequency, or alternatively with no tuning (also referred to as zero tuning). A used herein, zero tuning refers to tuning with the tuner frequency set to zero. The result of this is a third image, in addition to the images respectively corresponding to the low tuning frequency $\omega_L$ and the high tuning frequency $\omega_H$. The third image may be combined with the other images in step 225.

Accordingly, in a particular embodiment of the present invention, a third image may be acquired with no tuning, and a contrast agent may be added to the tissue of interest. The additional image with zero tuning represents the anatomy of the tissue with T1 weighting, which corresponds to the relaxation of the longitudinal magnetization of the tissue. When the tissue is imaged with a contrast agent, the image will then be used to determine the distribution of the contrast agent in the tissue. The combination of three images with low, high, and zero tunings is useful for revealing tissue deformation and contrast distribution simultaneously.

This embodiment may be used to image the viability of the heart muscle by showing regional function and tissue scars. The contrast agent leaves residues in dead tissue. As such, images showing the contrast agent correspond to the location of dead tissue within the imaged volume.

In order to best image dead tissue along with strain, the three images (high, low, and zero tuning) may be best acquired when the heart is under maximum deformation. The three images may be acquired after a delay relative to the reference time, and close to the end-systole of the heart's motion. For example, tagging may be done at end-diastole, and the three images may be acquired at end-systole.

The zero tuning image may be combined with the other images (anatomical and strain) to provide an image revealing function (from the strain image) and viability (from the zero tuning image). This combination provides an image depicting both function and viability as well as differentiation of fat and blood from dead tissue within the heart.

In combining the zero tuning image data with the anatomical and functional images in step 225, the software may implement a clustering technique to differentiate between different image components, including blood, contrast enhanced tissue, contracting tissue, and background.

Figure 16:
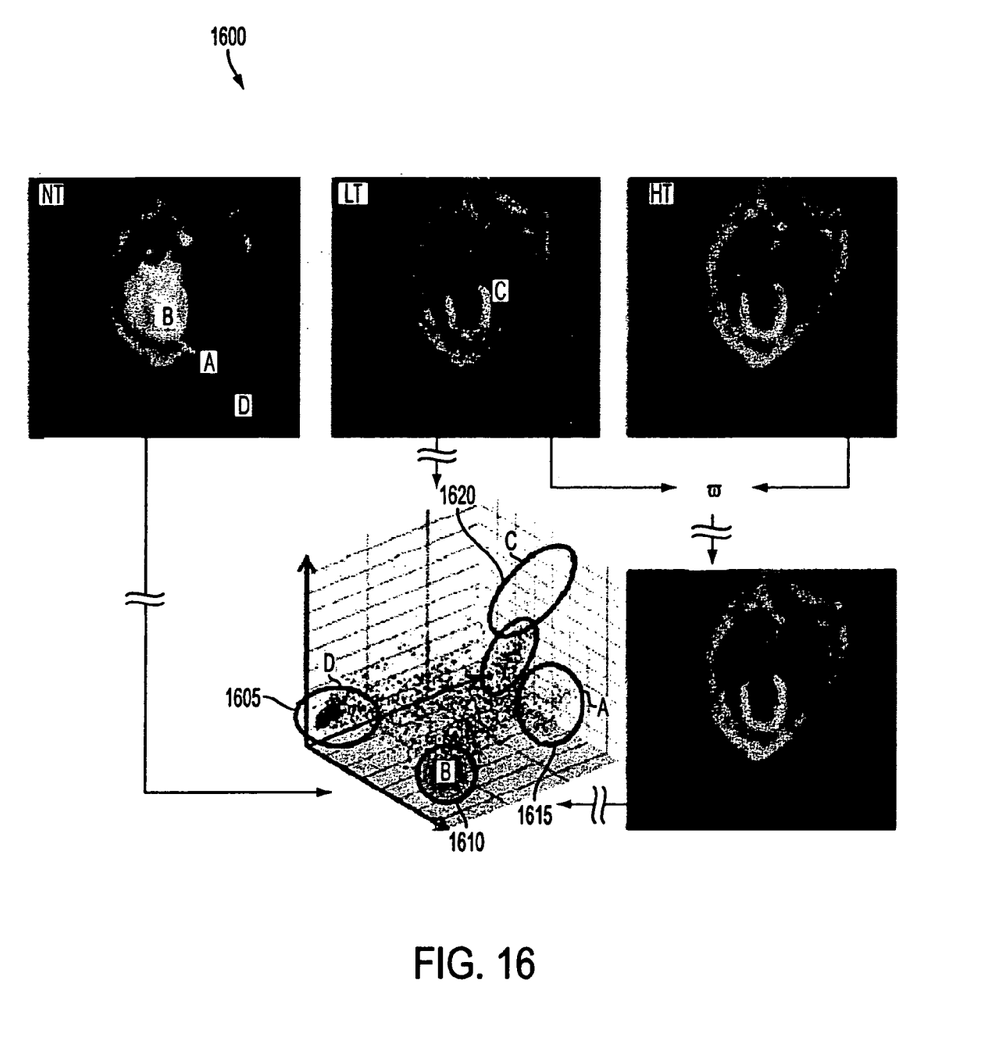
FIG. 16 illustrates an exemplary scatter plot for differentiating tissue according to the present invention.

FIG. 16 illustrates a hypothetical 3-D scatter plot 1600 of combined image data as assembled in step 225. Scatter plot 1600 contains clusters of data corresponding to blood 1620; contrast enhanced tissue 1615; contracting tissue 1620; and background 1605. Clustering algorithms, which are known to the art, may be implemented by the software to differentiate the above features in the combined images, and provide separate images of the differentiated features. The software may display the scatter plot, as well as any the images of differentiated features, on the user interface 175.

The present invention may be combined with other MRI techniques, such as first-pass perfusion, to provide tissue function information substantially without increasing the demand on the MRI system 100.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for acquiring strain images of tissue, comprising:
   transmitting a tagging pulse having a tagging spatial frequency;
   receiving a first RF signal corresponding to a first receive spatial frequency that is below the tagging spatial frequency;
   receiving a second RF signal corresponding to a second receive spatial frequency that is above the tagging spatial frequency; and
   computing a strain value corresponding to the received first RF signal and the received second RF signal.

2. The method of claim 1, wherein transmitting a tagging pulse comprises transmitting a slice-selection encoded gradient signal.

3. The method of claim 1, further comprising assembling a strain image based on the computed strain value.

4. The method of claim 1, wherein computing the strain value comprises:
   computing a first intensity corresponding to the received first RF signal;
   computing a second intensity corresponding to the received second RF signal;
   computing an estimated strain frequency based on the first intensity and the second intensity; and
   computing the strain value based on the strain frequency.

5. The method of claim 1, further comprising:
   computing a first plurality of pixel values corresponding to the received first RF signal;
   computing a second plurality of pixel values corresponding to the received second RF signal;
   computing a first plurality of intensity values based on the first plurality of pixel values;
   computing a second plurality of intensity values based on the second plurality of pixel values; and
   computing a plurality of strain values based on the first plurality of intensity values and the second plurality of intensity values.

6. The method of claim 5, wherein computing a plurality of strain values comprises computing a strain frequency based on the first plurality of intensity values and the second plurality of intensity values.

7. The method of claim 5, further comprising:
   combining the first plurality of pixel values and the second plurality of pixel values into an anatomical image.

8. The method of claim 7, further comprising combining the anatomical image with the plurality of strain values to form a colored functional image.

9. The method of claim 8, further comprising:
   receiving a third RF signal corresponding to a zero tuning;
   computing a third plurality of pixel values corresponding to the third RF signal; and
   combining the third plurality of pixel values with the colored functional image.

10. The method of claim 9, further comprising differentiating a plurality of tissue types, after combining the third plurality of pixel values with the colored functional image.

11. The method of claim 8, wherein differentiating the plurality of tissue types comprises differentiating blood, dead tissue, contracting tissue, and background.

12. The method of claim 1, wherein transmitting the tagging pulse comprises transmitting a 1D-1 SPAMM pulse sequence.

13. The method of claim 1, wherein transmitting the tagging pulse comprises transmitting a 1D-1D SPAMM pulse sequence.

14. The method of claim 1, wherein transmitting the tagging pulse comprises transmitting a 12D-1 SPAMM pulse sequence.

15. The method of claim 1, wherein transmitting the tagging pulse comprises transmitting a 1-SF SPAMM pulse sequence.

16. The method of claim 1, wherein transmitting the tagging pulse comprises transmitting a 1D-SF SPAMM pulse sequence.

17. The method of claim 1, wherein transmitting the tagging pulse comprises transmitting a 2D-SF SPAMM pulse sequence.

18. A system for acquiring strain imaging of a tissue, comprising:
- a gradient coil;
- an RF coil;
- an RF demodulator; and
- a processor having a computer readable medium encoded with a program for transmitting a tagging pulse having a tagging spatial frequency; receiving a first RF signal corresponding to a first receive spatial frequency that is below the tagging spatial frequency; receiving a second RF signal corresponding to a second receive spatial frequency that is above the tagging spatial frequency; and computing a strain value corresponding to the received first RF signal and the received second RF signal.

19. The system of claim 18, wherein the program for receiving a first RF signal corresponding to a first receive spatial frequency includes providing the first receive spatial frequency to the RF demodulator.

20. The system of claim 18, wherein the program comprises a program for assembling a strain image based on the computed strain.

21. The method of claim 18, wherein the program for computing the strain value comprises:
- a program for computing a first intensity corresponding to the received first RF signal;
- a program for computing a second intensity corresponding to the received second RF signal;
- a program for computing an estimated strain frequency based on the first intensity and the second intensity; and
- a program for computing the strain based on the strain frequency.

* * * * *